United States Patent [19]

Valan

[11] 3,957,966
[45] May 18, 1976

[54] STABILIZED VITAMIN FOOD COATINGS

[75] Inventor: Kent John Valan, Northampton, Pa.

[73] Assignee: GAF Corporation, New York, N.Y.

[22] Filed: Mar. 10, 1975

[21] Appl. No.: 556,972

Related U.S. Application Data

[63] Continuation of Ser. No. 254,897, May 19, 1972, abandoned.

[52] U.S. Cl. .................................... 424/33; 424/38; 424/45; 424/80; 424/201; 424/252; 424/255; 424/280; 424/284; 424/344; 426/72; 426/73; 426/94; 426/311; 426/496; 426/572

[51] Int. Cl.[2] ...................... A61K 9/32; A61K 9/42; A61K 9/58

[58] Field of Search ......... 260/33.4 R, 85.7, 88.3 L, 260/29.6 HN; 426/72, 73, 94, 311, 496, 572; 424/33, 38, 45, 80, 201, 252, 255, 280, 284, 344

[56] References Cited
UNITED STATES PATENTS

| | | | |
|---|---|---|---|
| 2,691,619 | 10/1954 | Bavley et al. | 424/80 X |
| 2,918,411 | 12/1959 | Hill | 424/80 |
| 3,037,911 | 6/1962 | Stoyle et al. | 424/38 |
| 3,080,292 | 3/1963 | Koff | 424/38 |
| 3,097,144 | 7/1963 | Banker | 424/33 |
| 3,136,695 | 6/1964 | Tansey | 424/22 |
| 3,148,124 | 9/1964 | Gaunt | 424/22 |
| 3,275,518 | 9/1966 | Endicott et al. | 424/33 X |
| 3,371,015 | 2/1968 | Sjogren et al. | 424/33 X |
| 3,553,313 | 1/1971 | Tort | 424/33 |
| 3,554,767 | 1/1971 | Daum | 426/6 |
| 3,584,114 | 6/1971 | Cavalli et al. | 424/38 |
| 3,767,825 | 10/1973 | Hammes et al. | 426/290 |

OTHER PUBLICATIONS

G.A.F. (1967) "PVP–An Annotated Bibliography–19-51–1966 Vol. I, II, III."

*Primary Examiner*—Shep K. Rose
*Attorney, Agent, or Firm*—Walter C. Kehm; Joshua J. Ward

[57] ABSTRACT

Food-fortifying, odor and taste masking melt-emulsion coating containing vitamins, polyvinylpyrrolidone, and selected fatty plasticizers for aerosol spray-on treatment, such as doughnut glaze or cake frosting of cereals and flour-based foodstuffs. The coating stabilizes foodstuffs otherwise adversely affected by light, oxygen, moisture or temperature of the environment.

25 Claims, No Drawings

STABILIZED VITAMIN FOOD COATINGS

This is a continuation of application Ser. No. 254,897, filed May 19, 1972 now abandoned.

BACKGROUND OF THE INVENTION

This invention relates to novel compositions of matter; and improved non-toxic carrier composition and more particularly it relates to improved pharmaceutical preparations providing for the release of pharmacologically active materials over a controlled extended period of time, methods of producing such preparations and stable aqueous emulsions derived therefrom.

It has now been found that a pharmaceutical oral dosage may be prepared in such a way as to enable the pharmacologically active material contained therein to be released on contact with the skin or to enable the active material contained therein to be released from the imbedded media or emulsion on ingestion at a retarded rate, thus prolonging the pharmacological activity and, at the same time, making it possible to accurately control the level of pharmacologically active material in the system so as to provide the desired effect. Among the inert components which are presently being used for such purposes are high molecular weight waxes, used singly or in various combinations, either evenly distributed among the active ingredients or first melted and then carefully coated over small particles of the active components (U.S. Pat. No. 2,918,411).

One disadvantge in the use of a wax for long-acting tablet formulations is that a relatively large mass of wax must be incorporated in the dosage form to give the desired long-acting effect. In other words, the ratio of wax to active component is a several-fold factor, thus requiring the manufacture of a bulky tablet such that its ingestion by patients is relatively difficult and uncomfortable.

It can be readily seen, however, that one of the prevailing problems in the pharmaceutical development field is the manufacture of controlled-release dosage forms which contain inert components that have large surface area, are nonabsorbable, and if absorbable, are substantially devoid of toxicity and undesirable side effects.

The use of alkaline earth metal salts of saturated fatty acids in tablet manufacture is known. These substances have been used for many years as tablet lubricants and fillers; they are incorporated into the final tablet granulation just prior to compression in relatively small quantities in order to facilitate compression of the granules without their adherence to the punches and dies in the tableting machine.

It is also known that saturated fatty acids, their esters, ethers and alcohols, can be pelletized with polyvinylpyrrolidone by converting the polymer, in the presence of the saturated fatty acid or its derivative, into a molten mass, granulating the congealed mss, reheating, cooling, adding the therapeutic component and pelletizing at a temperature near the set point.

It has now been surprisingly found that following the teachings of the instant invention, foods which are subjected to heat treatment in processing with an accompanying decrease in nutritive value due to partial or complete loss of carbohydrates, essential amino acids and vitamins may now be processed without losses. As is known, in order to compensate for the aforementioned losses, many nutritive components are added to food before processing is completed. Thus, most canned foods, evaporated milk products, dried protein products, cereals, and the like are fortified with amino acids, vitamins, etc. Some of these fortifying agents, however, are themselves affected by long periods (sterilization), light, moisture, oxygen or temperature of the environment.

Among the many disadvantages in using saturated fatty acids or their derivatives in combination with polyvinylpyrrolidone to prepare prolonged action dosage unit forms is their physical similarity to high molecular weight waxes. Because of their physical character, large quantities of the saturated fatty acid substance must be employed to obtain a desired effect. Thus, the proportion of polyvinylpyrrolidone to saturated fatty acid material must be about 1:7, or less. Moreover, it is known that saturated fatty acids themselves are inadequate as long acting vehicle agents, even though combined with polyvinylpyrrolidone. Thus, it has been equally necessary in order to obtain the desired prolonged effect, to incorporate a quantity of high molecular weight waxes, candelilla wax, bees wax or the like in the formulation. This adds further to the bulkiness of the dosage form, unnecessarily increasing the volume of the total mass and making the ingestion of same that much more difficult.

On the other hand, by using saturated fatty acid salts, while it is possible to decrease the ratio of salt to polyvinylprrolidone, one encounters the problem that there is an absence of complexing between the salt and the polyvinylprrolidone. This inherent drawback is immediately obvious where one seeks to produce an emulsion containing active ingredients, polyvinylpyrrolidone and a water insoluble hydrophobic chain end.

SUMMARY OF THE INVENTION

It is accordingly an object of the instant invention to obviate one or more drawbacks of the prior art.

It is still another object of the instant invention to prepare a polyvinylpyrrolidone powder melt and a stable aqueous emulsion derived therefrom.

It is a further object of the instant invention to provide for the entrapment of active components in the complex, which active components will have an extended shelf life, while at the same time providing a safe, ingestible or appliable composition.

It is yet a further object of the instant invention to provide for a composition which will prolong the active period of application of various externally applied compositions and thus provide sustained release thereof.

Further objects and advantages of the instant invention will be obvious as the description proceeds.

Broadly speaking, the instant invention includes the provisions of a composition comprising approximately by weight (a) 40–80 parts of a polymeric N-vinyl lactam or a copolymer of said N-vinyl lactam with up to about 70% vinyl acetate based on the weight of said copolymer, illustratively 50 to 90 parts by weight of N-vinyl lactam and about 50 to 10 parts by weight of said vinyl acetate (b) 20–60 parts of a plasticizing agent, (c) 0.05–40 parts of a medicinally active ingredient and (d) 0 to 99 parts solvent for components (a), (b) and (c); and a stable aqueous emulsion derived therefrom. The vinyl acetate when employed is included in said copolymer preferably in amounts of 10 to 50%, based on the weight of the copolymer, 0.1 to 70% being operative.

The composition may be prepared by heating the plasticizing agent, adding thereto components (a) and (c) to form a melt mass and thereafter allowing said mass to cool. The emulsion may thereafter be made from the thus formed composition. The composition may be used in emulsion or in melt blend form, i.e.,

| Melt Blend | Emulsion |
|---|---|
| Pharmaceutical pill | Milk of magnesia |
| Suppository | Opacified Soap |
| Lozenge | Opacified cosmetic |
| Hair treating composition | Silicone cream |
| Cosmetic stick | $TiO_2$ white shoe dressing |
| Absorbable surgical filament | Insecticidal Spray |
|  | Windshield antifog |
|  | Autopolish |
|  | Liniment |
|  | Cosmetic creme cold cream |
|  | Cosmetic lotion |
|  | Paper adhesive |
|  | Doughnut glaze |
|  | Chocolate candy |
|  | Cake frosting |
|  | Skin disinfectant |
|  | Hand lotion |
|  | Hair lacquer |
|  | Liquid face powder |

Exemplary plasticizing agents include unsaturated fatty acids, unsaturated fatty alcohols, ethers of unsaturated alcohols, partially acetylated glycerides and the like, E.g., included are the following: linoleic acid, oleic acid, linolenic acid, "Myvacet 7-00" (a partially acetylated monoglyceride, Distilled Product Industries).

The water soluble N-vinyl lactam monomer and the polymer derived therefrom as employed herein have the formulae:

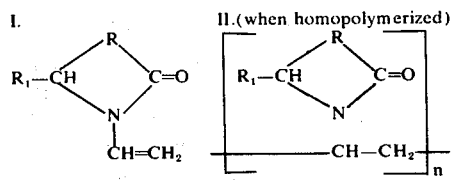

wherein R represents an alkylene bridge group necessary to complete a 5,6 or 7 membered heterocyclic ring system. $R_1$ represents either hydrogen or an alkyl group, and n represents a number indicative of the extent of polymerization and is usually at least 3 or 4, when homopolymerized.

All of the specific polymeric materials characterized by the foregoing general formula are commercially available and called polymeric N-vinyl lactams. They are obtained by polymerizing organic 5,6 or 7-membered ring compounds containing in their rings the —NH—CO-group, such as i.e., 1-vinyl-2-pyrrolidone, 1-vinyl-5-methyl-2-pyrrolidone, 1-vinyl-2-piperidone, N-vinyl-e-caprolactam, and the like. Depending upon the extent of polymerization, they have molecular weights ranging from at least 400 up to 2,000,000 or more. Viscosity measurements are commonly used as an indication of the average molecular weight of polymeric compositions, the instant polymers being characterized by a chain of carbon atoms to which the lactam rings are attached through their nitrogen atoms:

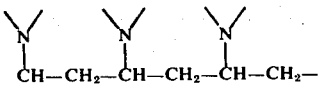

The K value (Fikenscher) of any particular mixture of polymers is calculated from viscosity data and is useful as an indication of the average molecular weight of such mixture. Its determination is fully described in "Modern Plastics," 23, No. 3, 157–61, 212, 214, 216, 218 (1945), and is defined as 1000 times $k$ in the empirical relative viscosity equation:

$$\frac{\log_{10} n_{rel}}{C} = \frac{75k^3+k}{1+1.5\ kc}$$

wherein $C$ is the concentration in grams per hundred cc. of polymer solution and $n_{rel}$ is the ratio of the viscosity of the solution to that of pure solvent. The K values are reported as 1000 times the calculated viscosity coefficient in order to avoid the use of decimals. For the purpose of the present invention, there may be employed those polymeric N-vinyl lactams having a K value of about 10 to 100, preferably of 15 to 90. If emulsions of higher viscosity are desired without increasing melt solids, polymers having a higher molecular weight may be employed, such as for the melt mix preparation.

K values and specific viscosities ($n_{sp}$) are interconvertible and are related through relative viscosity ($\pi_{rel}$). Thus, when viscosity measurements are taken on solutions which have a concentration of 1.00 gram of polymer per deciliter of solution at 25°C. (c=1), the relationships are as follows:

$$\pi_{rel} = n_{sp} + 1$$

Relative viscosity = specific viscosity plus one.
Relative viscosity = 10 [0,001K+0.000075K²/(1+0.015K)]
Hence, $n_{sp}$ = 10 [0.001K+0.000075K²/(1+0.0015K)]−1
Relative viscosity, specific viscosity and K are dimensionless, whereas inherent viscosity $$\frac{(\log_e n_{rel})}{C}$$

and intrinsic viscosity (the limit of inherent viscosity as C approaches zero) have the dimensions of dilution, i.e., the reciprocal of concentration.

The number of recurring polymer units enclosed by brackets in the foregoing general structural formula, indicated by $n$, or the extent of degree of polymerization, corresponds to a chain of roughly 4 to 20,000 monomer units or more. In actual practice, a mixture of polymeric molecules, each containing a different number ($n$) of monomer units, is always produced. The polymers are readily prepared by the procedural steps given in U.S. Pats. 2,265,450, 2,317,804, and 2,335,454 and in which working examples of all the species characterized by the above formula are given and all of which are incorporated herein by reference thereto.

DETAILED DESCRIPTION

The ratio of the N-vinyl lactam to the plasticizing agent may be varied depending upon what type of melt blend or emulsion is desired. For example, melts having more than 50% plasticizing agent form soft and more flexible films and thus are suitable for the coating of food substances or tablets. Melts prepared with high molecular weight polymeric N-vinyl lactams form strong and more rigid films and are more easily pulverized. The thickness of the emulsion is a function of the quantity of melt to solvent; rather than the amount of polymer in the melt. In the same manner, the emulsion viscosity may be kept quite low so as to enable it to pass through the nozzle of an aerosol spray can.

Broadly speaking, one aspect of the invention comprises blending the poly (N-vinyl lactam) (PVL), such as for instance, poly (N-vinyl pyrrolidone) or copolymer of an N-vinyl lactam and vinyl acetate melt in hot water while vigorously mixing, thereby resulting in a melt-water emulsion. The quality of emulsion will depend on the temperature of the water, agitation and the type of melt. Water-melt emulsions can be prepared either directly by adding the hot melt to hot water or indirectly by adding pulverized melt material into hot water. Melts can also be emulsified in lukewarm or cold water; however, this method takes a longer period of time and requires more mechanical stirring. Furthermore, such emulsions (the latter) are not as stable as emulsions prepared at 90°–100°C (they tend to separate more quickly).

Preferably the components blended in hot melts or entrapped in cold melt matrixes are emulsified together with the melt. The physical properties of such emulsions will depend on the ratio of melt to water and the type and amount of unsaturated fatty material used in the original melt. Emulsions containing 40 or more percent of emulsified melt can be considered heavy viscosity lotions or creams. Emulsions containing less than 40% solids will be considered liquid lotions or low viscosity aqueous emulsions.

Emulsion stability and emoliency characteristics will definitely depend on the type of melt that is being emulsified. A "melt" composed of a poly (N-vinyl lactam) and partially acetylated glycerides or fatty acids will form better emulsions than the one made from the corresponding alcohols or ethoxylated alcohols. Branched chain fatty acids form better emulsions than linear analogues of the same fatty acids; also unsaturated fatty acids form better emulsions than the saturated acids. Emulsion stability, emoliency and the like also depend on the poly (N-vinyl lactam) —unsaturated fatty component ratio in the melt. The best emulsions are obtained when the unsaturated fatty component concentration is the same as or less than the concentration of poly (N-vinyl lactam) or copolymer. Melts having a high concentration of the "fatty" component do not form stable emulsions. Thus stable emulsions are obtained when the composition of the melt preferably is 40–80% poly (N-vinyl lactam) or a copolymer of VP/VA and 60–20% unsaturated fatty component.

As with poly (N-vinyl lactam) or copolymer melts, melt emulsions are primarily designed for pharmaceutical and veterinary applications. However, they can be useful in: (1) the food industry, especially in the treatment of cereal and (flour) baked food stuffs, (2) cosmetic-emulsions can be used (directly or modified) as moisturizing, conditioning skin preparations in the form of lotions or creams; also emulsions are good opacifying compounds for various cosmetic preparations such as cream rinses, cream conditioners, etc.

Additional applications include:

1. Various pharmaceutical components such as vitamins, aspirin, MgO, etc., can be entrapped in safe and stable emulsions.
2. Components entrapped in melt emulsions may mask unacceptable odor or taste.
3. Vitamins and other nutritive agents can be imbedded in melts.
4. Emulsions so prepared can thereafter be sprayed on cereal and other food stuff.
5. Melt emulsions should be acceptable to U.S. Food & Drug Administration for use in edible mixtures.
6. Melt emulsions can be applied as a cream or lotion by itself, or formulated with other components.
7. Emulsions can be used as safe opacifiers in food, beverage, or cosmetic applications.

One may employ 70 parts of poly (N-vinyl lactam) or copolymer to about 30 parts of plasticizing agent, however, the ideal ratio is about 55–45. In the emulsion, the ratio may be 1:1:98 (PVL/Plasticizer/water) to 40:40:20 (PVL/Plasticizer/water).

The novel combination of the present invention, comprises, as the principle substituents of formulation, one or more thereapeutic ingredients distributed throughout a molecularily dispersed poly (N-vinyl lactam) or copolymer phase, and forming a network about a water insoluble, hydrophobic, unsaturated fatty acid or fatty component macrophase, the poly (N-vinyl lactam)-fatty acid constituents being in the ratio of about 0.5:1 to 4:1 of poly (N-vinyl lactam): plasticizing agent when employed in the form of the melt. The active component is dissolved or dispersed into the molten poly (N-vinyl lactam-plasticizing mass just before the mass is removed from heating. Upon cooling, the molten mass forms a solid film which may later be granulated into a powder or directly emulsified. It will be observed that the ratio of poly (N-vinyl lactam) or copolymer to unsaturated acid component is not critical, and may be varied over a substantial range, depending upon the rate of release of the active component desired. When the above ratio is from about 1 to about 0.5 to 1, release of the active ingredient is obtained in approximately a couple of hours. When the ratio is about 1 to about 1.5 to 2.0, the incorporated active ingredient is released over a longer period of time, approximately over five hours. When the ratio is from about 1 to about 3 to 4, release is obtained over a much longer period of time, approximately 12 to 24 hours. Of course, all the foregoing times may be affected by a variety of variables, such as ingredient, variation of components and the like.

Although the mechanism whereby gradual release of the active ingredient is attained over an extended time period from the novel combination of this invention has not absolutely been determined, it is believed with reasonable certainty that the desired effect is achieved because of the peculiar physical combination of components, compatability, solubility parameters and a co-action during absorption on the surface to which same has been applied.

When preparing the emulsion, the combination of the instant invention comprises, in a general way, the addition of the melt to a sufficient volume of water to wet (disperse or emulsify) the dry melt containing the prescribed quantity of unsaturated fatty acid component-poly (N-vinyl lactam) or copolymer and active ingredient as well as any other constituents, if desired. The active ingredient dissolved in the added water, when water soluble, becomes evenly distributed throughout the poly (N-vinyl lactam) or copolymer aqueous phase. On the other hand, where the active ingredient is insoluble in water it will become dispersed throughout the non-aqueous phase with the unsaturated fatty acid component. The active ingredient-poly (N-vinyl lactam) or copolymer water system will flow easily about the hydrophobic fatty acid microparticles. On the other hand, the active ingredient-hydrophobic unsaturated fatty acid component micro particles will be evenly dispersed throughout the poly (N-vinyl lactam) or copolymer aqueous system.

When the above described composition comes in contact with the digestive juices, the aqueous medium infiltrates the hydrophobic fatty acid component mass at a slow, constant rate by following the network path of the hydrophilic polymeric film through capillary action. The molecules of reactive ingredient are dissolved in the digestive juices at the point of contact of the latter with the drug containing polymeric film. The dissolved active ingredient is then free to diffuse into the body and the surrounding area and is available for absorption. Because of this method of diffusion of drug out of the emulsion there is no rupture of the fatty acid mass, and the composition is operative to function as an inert carrier for the active ingredients.

It should be born in mind that whether by solid or by emulsion, there are essentially two competing forces operating within this composition as it travels the intestinal tract and is bathed in the aqueous fluid, namely, the hydrophobic barrier of the unsaturated fatty acid component and the surrounding hydrophilic film of the polymer and active component. As a result, the dissolution of water soluble therapeutics is readily controlled by increasing or decreasing the quantity of hydrophobic material in the composition. In other words, by adding a relatively high proportion of fatty acid component, as compared to polymer, the active ingredients will be released over a long period of time. Conversely, by decreasing the ratio, the therapeutic component is released over a shorter period of time. Advantage is thus taken of the unique hydrophilic, nonswelling film forming properties of the poly (N-vinyl lactam) or copolymer thereof as contrasted to the action of other commonly used components which do not possess such physical properties. It should also be born in mind that where the active ingredient is not water soluble, the unique ability of the polymer to complex with the fatty acid component and thus produce an emulsion therefrom affords the composition the opportunity to remain substantially uniformly dispersed throughout an emulsified phase wherein the active ingredient is in the non-aqueous phase.

It will be readily apparent, therefore, that the novel composition herein lends itself to a wide variety of applications in the pharmaceutical field since it provides a method for administering water soluble and water insoluble therapeutics singly or in admixture with other substances, over a controlled period of time with predictable regularity and time lag. Drugs which are suitable for use in the novel composition include antihistamines, central nervous system depressants, central nervous systems stimulants, vitamins, antibiotics, antacids, cough depressants, etc. These may be incorporated into the novel composition either in the form of water insoluble bases or as their water soluble salts, depending upon the particular mode of absorption found most advantageous.

It is to be emphasized, that, although the unsaturated fatty acid is used as a critical component in the instant composition, the quantity thereof is incorporated in the melt mixing process. That is to say, it is first melted and thereto there is added the polymeric material along with the other ingredients and it thereby becomes an integral component of the composition.

There is no restriction on the inclusion of other commonly employed excipients in the formulation of the novel combination of this invention. Thus, one may employ as diluents in whatever quantities are indicated, such components as dibasic calcium phosphate, lactose, mannitol, and others. One may also include as binders, such gums as acacia, or tragacanth.

The following examples are intended to illustrate but not to limit the scope of the present invention. All parts and proportions herein as well as in the appended claims are by weight unless otherwise indicated.

GENERAL PROCEDURE FOR PREPARING MELTS

The plasticizing agent (fatty alcohol - unsaturated fatty acid-, partially acetylated glyceride, or ethoxylated fatty alcohols or mixtures of these components) is heated to 120°–150°C, a polymeric N-vinyl lactam (PVL), i.e., a polymeric N-vinyl lactam (PVP, K 29-32, K-30, or 90) or VP/VA copolymer is slowly added while stirring. When all of the polymeric lactam is added, stirring is continued for several more minutes, then the component to be imbedded is added to the molten mass, stirred several minutes longer, transferred to a dish or pan and allowed to cool. The solid matrix is then broken up into smaller pieces and pulverized on the mill. The composition of the melt can be summarized in the following formula:

| | |
|---|---|
| PVP or copolymer of VP/VA | 40–80 parts |
| Plasticizing component | 20–60 |
| Active component | 0.05–50 |

It is difficult to dissolve greater than 70 parts of PVP alone or VP/VA into 30 parts of plasticizing agent. The ideal ratio, therefore, is 55 parts of PVP to 45 parts of plasticizer.

The copolymer of vinyl pyrrolidone and vinyl acetate may be prepared in accordance with techniques known in the art.

PREPARATION OF MELT EMULSIONS

1. Hot Melt to Hot Water Procedure

A quantity of distilled water is brought to boil, 80 gm. thereof is weighed into a beaker and then transferred to a Waring blender jar which is heated by a heat gun directed at the base of the jar. 20 gms. of hot melt (100°C. or over) is transferred to the rapidly agitating Waring blender and stirring is continued for 10 minutes. The Waring blender is then stopped and the emulsion transferred to a jar.

PULVERIZED MELT TO HOT WATER

The procedure for preparing emulsions from powdered solids is similar to that above. Instead of adding hot melt, pulverized material is added slowly while vigorously mixing under constant heat. When all the pulverized material has been added, stirring is continued for 10 more minutes. The emulsified material is then transferred to a jar.

COMPARATIVE EXAMPLES

Investigation of PVP-Stearyl Alcohol Melt Characteristics

Example A

7 gm. Polyvinyl pyrrolidone (PVP) is dissolved in melted stearyl alcohol (63 g.) with stirring until it congeals. The congealed mass is cooled to room temperature, broken up and passed through a No. 10 mesh screen and No. 16 mesh screen.

Example B

The procedure of Example A is repeated with twice the amount of PVP, leaving the amount of stearyl alcohol the same. Ratio --1:4.5 PVP: stearyl alcohol.

Results: PVP dissolves readily at 70°C. Half a portion of this melt is allowed to solidify; the other half is further heated to 145°C. then allowed to cool. The melt mass appeared to be homogeneous at both temperatures.

Example C

A PVP-stearyl alcohol ratio of 1:2.25 is used. The PVP herein did not melt as readily and completely at 70°C. The 70°C. melt matrix herein is a slurry of unmelted granular PVP in stearyl alcohol. The PVP melt at 140°C. temperature is homogeneous in the molten and solid state.

Example D

A PVP-stearyl alcohol ratio of 1:1. is used. At 70°C. only a portion of PVP melt material appears to be compatible in the slurry. A cooled melt-matrix contains a large portion of granular PVP.

At 140°C. all PVP melts and forms a homogeneous, transparent mass. Upon cooling, it forms a smooth, translucent matrix.

Compatability data of PVP-stearyl alcohol melts with a candelilla wax ratio of 7:8 PVP melt: candelilla wax at 80°C is found below.

TABLE I

| PVP/Stearyl Alcohol Ratio | PVP Melt Preparation Temp., °C. | Compatibility Data of PVP Melt and Candililla Wax |
|---|---|---|
| 1:9 | 70 | compatable |
| 1:9 | 140 | " |
| 1:4.5 | 70 | " |
| 1:4.5 | 140 | " |
| 1:2.5 | 70 | incompatable |
| 1:2.5 | 140 | " |
| 1:1 | 70 | " |
| 1:1 | 140 | " |

Preparation of PVP-stearyl alcohol emulsions from PVP melts are described in Table II.

TABLE II

| PVP/Stearyl Alcohol Ratio | PVP Melt Preparation Temp., °C. | Appearance of Emulsion |
|---|---|---|
| 1:9 | 70 | Didn't form emulsion. Two separate layers. |
|  | 140 | Same as above |
| 1:4.5 | 70 | Same as above |
|  | 140 | Same as above |
| 1:2.5 | 70 | Some emulsified product but bulk of stearyl alcohol precipitated. |
|  | 140 | Same as above |
| 1:1 | 70 | Same as above |
|  | 140 | Completely homogeneous and smooth emulsion. |

Example I

| | |
|---|---|
| Partially acetylated monoglyceride (Myvacet 7-00) | 45 g. |
| PVP K 29-32 | 55 g. |
| Vitamin "C" (Merck) | 10 g. |

Melt Preparation

A beaker containing the plasticizer (Myvacet) is placed into an oil bath. The plasticizer is heated to 145°–153°C, the PVP is sifted into the plasticizer over a 10 minute period while stirring constantly. It is allowed to stand for about 2 minutes, the vitamin is then added over a 1–2 minute period. The mixture is immediately cast as a film onto a Mylar sheet and allowed to cool. Break the thus formed melt into small pieces, place same into a blender along with a small quantity of dry ice. Grind for several minutes or until the melt becomes granular or powdery. Transfer to a Petri dish, and place in a dessicator to dry the contents and to prevent moisture formation.

PREPARATION OF MELT EMULSION

A blender jar is placed on the blender base and a heat gun directed to the base of the jar. A 10 gm. portion of pulverized melt is weighed out and set aside. A flask containing distilled water is heated to the boil, 40 gms. of boiling water is then transferred immediately to the blender jar. Portions of the pulverized melt are added step-wise, mixing after each addition, until all the pulverized melt has been added. The blender is run for about 10 minutes after the melt addition is completed.

The temperature of the emulsion is about 80°C. after mixing.

Example 2

The procedure of Example 1 is followed for both the preparation of the melt and emulsion. The ingredients of the melt are varied as follows.

| | |
|---|---|
| Stearic Acid (food grade) | 45 g. |
| PVP (K-29-32) | 55 g. |

| Riboflavin (Merck) | 1 g. |

Example 3
The procedure of Example 1 is followed for both the preparation of the melt and emulsion. The ingredients of the melt are varied as follows.

| Partially acetylated monoglyceride (Myvacet) | 45 g. |
| PVP (K 29-32) | 55 g. |
| Thiamin (Merck) | 10 g. |

Example 4
The procedure of Example 1 is followed for both the preparation of the melt and emulsion. The ingredients of the melt are varied as follows and they are pulverized using a Wiley Mill.

| Stearic Acid | 45 g. |
| PVP (K 29-32) | 55 g. |
| Cyanocobalamin (Vitamin $B_{12}$), (Merck) | 1 g. |

Example 5
The procedure of Example 1 is followed for both the preparation of the melt and emulsion. The ingredients of the melt are varied as follows and they are pulverized using a Wiley Mill.

| Stearic Acid | 45 g. |
| PVP (K 29-32) | 55 g. |
| Aquapalm (Vitamin A Palmitate), (Hoffman-La Roche) | 1 g. |

Example 6
The procedure of Example 1 is followed for both the preparation of the melt and emulsion. The ingredients of the melt are varied as follows and they are pulverized using a Wiley Mill.

| Stearic Acid | 45 g. |
| PVP (K 29-32) | 55 g. |
| di-Alpha Tacophenyl Acetate NF-FCC (Vitamin E.Acetate) (Hoffman-La Roche) | 1 g. |

Example 7
The procedure of Example 1 is followed for both the preparation of the melt and emulsion. The ingredients of the melt are varied as follows.

| Partially acetylated monoglyceride (Myvacet) Polyvinyl pyrrolidone | 60 g. |
| PVP (K-90) | 40 g. |

Example 8
The procedure of Example 1 is followed for both the preparation of the melt and emulsion. The ingredients for both are varied as follows.

| Stearic Acid | 70 g. |
| PVP (K-90) | 30 g. |

Example 9
The procedure of Example 1 is followed for both the preparation of the melt and emulsion. The ingredients for both are varied as follows.

| Partially acetylated monoglyceride (Myvacet) | 45 g. |
| Copolymer of vinyl pyrrolidone/ vinyl acetate (PVP/VA) | 55 g. |

Example 10
The procedure of Example 1 is followed for both the preparation of the melt and emulsion. The ingredients for both are varied as follows.

| 1-1-Octadecanol | 50 g. |
| PVP (K-30) Polyvinyl pyrrolidone | 50 g. |

Example 11
The procedure of Example 1 is followed for both the preparation of the melt and emulsion. The ingredients for both are varied as follows.

| Isostearic Acid | 45 g. |
| PVP (K 29-32) | 55 g. |

Example 12
The procedure of Example 16 is followed for the preparation of the melt except oleic acid is used instead of ("Myvacet"). The procedure for the emulsion is as follows.

Bring a quantity of distilled water to boil, weigh out 400 g. thereof and transfer to a preheated blender jar. Add the hot melt directly to the water and mix for 10 minutes and thereafter transfer the emulsion to a clean jar.

| Oleic Acid | 45 g. |
| PVP (K 29-32) | 55 g. |

Example 13
The procedure of Example 1 is followed for the preparation of the melt except isostearic acid was used instead of (Myvacet 7-00). The procedure for the emulsion is the same as that followed in Example 16 but with the use of 150 g. $H_2O$ (40% Emulsion-thicker and creamier than Example 12–20% Emulsion).

| Isostearic Acid | 45 g. |
| PVP (K 29-32) | 55 g. |

Example 14
The procedure for the preparation of the melt is the same as in Example 1 except oleic acid was used instead of (Myvacet). The procedure for the emulsion is the same as that followed in Example 12 but with the use of 66 g. H₂O (60% Emulsion - very thick, creamy, smooth).

| Oleic Acid | 45 g. |
|---|---|
| PVP (K 29-32) | 55 g. |

EXAMPLE 15

Similar to Ex. 12 except with a substitution of linoleic acid for the oleic acid.

EXAMPLE 16

Similar to Ex. 12 except with a substitution of linolenic acid for the oleic acid.

The terms "unsaturated fatty acid component, unsaturated fatty component, and fatty acid component" as employed herein are intended to generically include any of the plasticizing agents operative herein, except when mentioned for comparative purposes.

Proof of Complex Formation by Infra Red Spectrophotometry

In order to establish a formation of a complex between PVP (K30)-fatty acid, alcohols, partially acetylated monoglycerides etc, infrared examination was made using alcohol and chloroform solutions and physical blends of PVP-fatty compounds, to establish if there was any frequency shift.

All samples in Table III, except sample 1, are a 30% solution in undenatured alcohol or chloroform, of a mixture of 45% each of the various fatty acids, or alcohols a partially acetylated monoglyceride and 55% PVP (K-30). The solutions are prepared by adding separately the PVP and the other component to the solvent.

Sample 1 is a reference standard consisting of a solution in undenatured alcohol of PVP (K-30) only.

Infrared spectrum was obtained on each sample in Table 3 in the liquid (solution) and solid state (film). The film is obtained by evaporating the solution on a CsBr window at 100°C, for five minutes in a vacuum oven.

The reference sample 1 of PVP (K-30) shows no shift in frequency (actual position of absorption band cm.$^{-1}$) when recorded as a solution or film while all the other samples[1] exhibit a change in frequency when recorded as films.

[1]Except isostearyl alcohol + 3 E₀O₀ om CHCl₃.

Samples in Table IV were prepared by the KBr technique; i.e., the sample is finely ground and mixed with KBr(powder), then compacted under pressure to form a clear pellet.

A reference sample of PVP (K-30) alone absorbs at 1650 cm$^{-1}$. PVP (K-30) itself, also absorbs at 1650 cm$^{-1}$.

An external blend, by Waring blender of 45% stearyl alcohol and 55% PVP K-30 also absorbs at 1650 cm$^{-1}$ but a similar blend prepared by melting the two components absorbs at a higher frequency (1660 cm$^{-1}$).

A melt blend of various concentrations of Myvacet 7-00 and PVP K-90 shows an increase in frequency as the PVP K-90 concentration increases.

At the 100% PVP K-90 level there is no frequency shift.

TABLE III

Infrared Spectroscopy Data of PVP/Plasticizer Blends

| Sample | Description | Solvent | Position of Absorption Bands[2] | |
|---|---|---|---|---|
| | | | Solution cm$^{-1}$ | Film cm$^{-1}$ |
| 1. | PVP K-30 (100%) | Ethanol[1] | 1652 | 1651 |
| 2. | Stearic acid+PVP (K-30) | " | 1650 | 1669 |
| | Isostearic acid+PVP(K-30) | " | 1650 | 1662 |
| | Oleic acid+PVP(K-30) | " | 1650 | 1668 |
| | Linoleic aicd+PVP(K-30) | " | 1650 | 1660 |
| | Myristic acid+PVP(K-30) | " | 1650 | 1661 |
| 3. | Stearyl alcohol+PVP(K-30) | " | 1650 | 1653 |
| | Isostearyl alcohol+PVP(K-30) | " | 1650 | 1660 |
| | Cetyl alcohol+PVP(K-30) | " | 1650 | 1660 |
| | Oleyl alcohol+PVP(K-30) | " | 1650 | 1660 |
| | Isostearyl+1 EO+PVP(K-30) | " | 1650 | 1660 |
| | Isostearyl+3 EO+PVP(K-30) | " | 1650 | 1665 |
| | Isostearyl+5 EQ+PVP(K-30) | " | 1650 | 1662 |
| 4. | Myvacet 7-00+PVP(K-30) | " | 1650 | 1662 |
| 5. | Stearic acid+PVP(K-30) | CHCl₃ | 1655 | 1670 |
| | Linoleic acid+PVP(K-30) | " | 1652 | 1663 |
| | Isostearyl alc.+3 EO+PVP (K-30) | " | 1652 | 1645 |
| | Myvacet 7-00 | | None | None |

[1]undenatured alcohol
[2]-CON-band of PVP K-30

TABLE IV

Infrared Spectroscopy Data on PVP/Plasticizer Physical and Melt Blends Employing KBr Technique

| Sample | Description | Position of Absorption Band (cm$^{-1}$)[1] | |
|---|---|---|---|
| 6. | Melt blend of 45% stearyl alcohol+55% PVP (K-30) | 1660 | |
| 7. | PVP (K-30) | 1650 | |
| | PVP (K-29-32) | 1650 | |
| 8. | External blend, Waring blender, 50% stearyl alcohol+55% PVP (K-30) | 1645 | |
| 9. | External blend, Waring blender, 45% stearyl alcohol+55% PVP (K-30) | 1650 | |
| 10. | Melt blend of 90% Myvacet* 7-00+10% PVP (K-90) | 1640 | |
| | Melt blend of 80% Myvacet* 7-00+20% PVP (K-90) | 1649 | |
| | Melt blend of 70% Myvacet* 7-00+ 30% PVP (K-90) | 1660 | complexing |
| | Melt blend of 60% Myvacet* 7-00+ 40% PVP (K-90) | 1661 | |

TABLE IV-continued

| Infrared Spectroscopy Data on PVP/Plasticizer Physical and Melt Blends Employing KBr Technique | |
|---|---|
| Sample Description | Position of Absorption Band (cm$^{-1}$)[1] |
| Melt blend of 0% Myvacet* 7-00+100% PVP (K-90) | 1640 |

[1]-CON-band of PVP K-30 or K-90 comparable with film values of Table 1
*Distilled Acetylated Monoglyceride derived from hydrogenated lard in which about 2/3 of the free OH groups are acetylated. Distillation Products Industries, Division of Eastman Kodak Company. Kodak/DPI Product Bulletins A-1 (6/15/72) and ZA-22 (1969)

It can be concluded from the data in Tables III and IV that some complexing results between mixtures of PVP and various compounds such as fatty alcohols, oxyethylated alcohols, fatty acids, partially acetylated monoglycerides. No complexing takes place in externally blended PVP/fatty acid films made from solutions and samples which have been merely blended (Table III and Table IV).

Furthermore, as can readily be determined from working examples 1–6, a complex is formed at a temperature above 100°C, about 130°C, to which the fatty acid or fatty derivative is heated prior to the addition of the poly (N-vinyl pyrrolidone). As was readily apparent, where there is no heating above 100°, there occured no complexing between the fatty acid and the poly (N-vinyl-pyrrolidone). Furthermore, the stable aqueous emulsions are formed from the most unsaturated acids, e.g. linoleic acid, linolenic acid, oleic acid, lastly the poorest emulsions were formed from the saturated fatty acid and fatty acid derivative.

Having thus described my invention, what I claim as new and desire to be secured by Letters Patent, is as follows:

1. A food-fortification, odor and taste masking, vitamin-stabilizing melt emulsion coating composition comprising approximately by weight (a) about 40 parts to 80 parts of a polymer, said polymer consisting essentialy of (1) a homopolymer of N-vinylpyrrolidone or (2) a copolymer of said N-vinylpyrrolidone with up to about 70 percent vinyl acetate based upon the weight of said copolymer; said homopolymer or copolymer having a K value of about 10 to 100; and (b) in complex combination with about 70 parts to 30 parts of a plasticizer which is stearyl alcohol, partially acetylated monoglyceride, stearic acid, isostearic acid, oleic acid, 1-octadecanol, linoleic acid or linolenic acid; and (c) about 0.5 to 50 parts of a vitamin thereby having extended shelf life imparted thereto, said vitamin otherwise adversely afeected by light, moisture, oxygen, or temperature of the environment, said vitamin being selected from the group consisting of vitamins A, $B_1$, $B_2$, $B_{12}$, C and E.

2. A composition as claimed in claim 1 for oral ingestion and comprising a stable aqueous emulsion thereof.

3. A composition as claimed in claim 1 comprising an aqueous emulsion thereof wherein water is present in a ratio, by weight of said polymer, plasticizer and water, of about 20 percent to 98 percent.

4. A composition as claimed in claim 3 wherein said plasticizer and polymer in said complex combination are incorporated with said water in the form of a melt.

5. A composition as claimed in claim 4 wherein said plasticizer is oleic acid.

6. A composition as claimed in claim 4 wherein said plasticizer is a partially acetylated monoglyceride.

7. A composition as claimed in claim 4 wherein said polymer and said plasticizer in said complex combination are present in a ratio by weight to each other of about 1 to 1.

8. A composition as defined in claim 1 wherein said copolymer is composed of about 50 to 90 parts of said N-vinylpyrrolidone and about 50 to 10 parts of said vinyl acetate.

9. A composition as defined in claim 1 wherein component (a) is poly (N-vinyl pyrrolidone).

10. A composition as defined in claim 1 wherein said vitamin is water soluble.

11. A composition as defined in claim 1 wherein said vitamin is water insoluble.

12. An aerosol spray containing a propellant and a composition as defined in claim 1.

13. A composition as claimed in claim 1 and including a pharmaceutically acceptable solvent.

14. A composition as claimed in claim 1 wherein plasticizer is stearic acid.

15. A composition as claimed in claim 1 wherein said plasticizer is linoleic acid.

16. A composition as claimed in claim 1 wherein plasticizer is linolenic acid.

17. A composition as claimed in claim 1 wherein plasticizer is stearyl alcohol.

18. A composition as claimed in claim 1 wherein plasticizer is isostearic acid.

19. A composition as claimed in claim 1 wherein said plasticizer is 1-octadecanol.

20. A composition as claimed in claim 1 wherein vitamin is vitamin A.

21. A composition as claimed in claim 1 wherein vitamin is vitamin E.

22. A composition as claimed in claim 1 wherein vitamin is vitamin C.

23. A composition as claimed in claim 1 wherein vitamin is vitamin $B_{12}$.

24. A composition as claimed in claim 1 wherein vitamin is vitamine $B_2$.

25. A composition as claimed in claim 1 wherein said vitamin is vitamin $B_1$.

* * * * *